US012697033B2

(12) United States Patent
Nakamura

(10) Patent No.: US 12,697,033 B2
(45) Date of Patent: Aug. 4, 2026

(54) SCREENING APPARATUS FOR COLD SYNDROME-POSITIVE PEOPLE

(71) Applicant: Hiroshi Nakamura, Iwakuni (JP)

(72) Inventor: Hiroshi Nakamura, Iwakuni (JP)

( * ) Notice: Subject to any disclaimer, the term of this patent is extended or adjusted under 35 U.S.C. 154(b) by 328 days.

(21) Appl. No.: 18/570,779

(22) PCT Filed: May 29, 2023

(86) PCT No.: PCT/JP2023/019875
§ 371 (c)(1),
(2) Date: Dec. 15, 2023

(87) PCT Pub. No.: WO2023/238717
PCT Pub. Date: Dec. 14, 2023

(65) Prior Publication Data
US 2024/0277232 A1 Aug. 22, 2024

(30) Foreign Application Priority Data

Jun. 6, 2022 (JP) ................................. 2022-091803

(51) Int. Cl.
*A61B 5/01* (2006.01)
*A61B 5/00* (2006.01)
(52) U.S. Cl.
CPC .............. *A61B 5/01* (2013.01); *A61B 5/7246* (2013.01)
(58) Field of Classification Search
CPC ....... A61B 5/01; A61B 5/7246; A61B 5/4854; A61B 5/6815; A61B 5/0532; G16H 70/40;
(Continued)

(56) References Cited

U.S. PATENT DOCUMENTS 6,511,437 B1    1/2003  Nakamura
8,007,436 B2    8/2011  Katayama
(Continued)

FOREIGN PATENT DOCUMENTS

CN        111182470 A      5/2020
JP        2001-137196 A    5/2001
(Continued)

OTHER PUBLICATIONS

Barrett B, Brown RL, Mundt MP, Thomas GR, Barlow SK, Highstrom AD, Bahrainian M. Validation of a short form Wisconsin Upper Respiratory Symptom Survey (WURSS-21). Health Qual Life Outcomes. Aug. 12, 2009;7:76. (Year: 2009).*

(Continued)

*Primary Examiner* — Jacqueline Cheng
*Assistant Examiner* — Jonathan E. Cooper
(74) *Attorney, Agent, or Firm* — Fleit Intellectual Property Law; Paul D. Bianco

(57) ABSTRACT

A screening apparatus for cold syndrome-positive people includes an EIFU temperature measurer having right and left temperature measuring parts; a calculation unit of that calculates a difference value between a right and left EIFU temperatures measured with the right and left temperature measuring parts; an input unit of left/right discomfort to which right discomfort information and left discomfort information on discomfort in a right pharynx region and a left pharynx region perceived by the cold syndrome positive person are input; a calculation unit of left/right discomfort that calculates a degree of coincidence between the right discomfort information and the left discomfort information; an evaluation unit that outputs information of severity based on the calculated difference value and the degree of coincidence; and a reporting unit that notifies severity of the cold (Continued)

syndrome-positive person based on the information of severity.

2 Claims, 5 Drawing Sheets

(58) Field of Classification Search
    CPC ........ G16H 20/10; G16H 50/20; G16H 50/30; G16H 50/80; G01K 13/20
    USPC ......................................................... 600/549
    See application file for complete search history.

(56)                     References Cited

U.S. PATENT DOCUMENTS

| | | | |
|---|---|---|---|
| 2010/0113894 A1 | 5/2010 | Padiy | |
| 2018/0256106 A1* | 9/2018 | Rogers | G01J 5/0011 |
| 2020/0245873 A1 | 8/2020 | Frank | |
| 2021/0311055 A1* | 10/2021 | McDevitt | G01N 33/548 |
| 2021/0333153 A1 | 10/2021 | Xie | |
| 2023/0248320 A1* | 8/2023 | Lafon | A61B 5/742 600/549 |
| 2023/0326567 A1* | 10/2023 | Asthana | G16H 10/60 705/2 |
| 2023/0329561 A1* | 10/2023 | Cui | A61B 5/015 |

FOREIGN PATENT DOCUMENTS

| | | | |
|---|---|---|---|
| JP | 2010-531154 A | 9/2010 | |
| JP | 5656978 B2 | 1/2015 | |
| JP | 2021-074464 A | 5/2021 | |
| JP | 6951526 B1 | 10/2021 | |
| JP | 2021-171623 A | 11/2021 | |
| WO | 2004/089202 A | 10/2004 | |
| WO | 2011/125349 A1 | 10/2011 | |
| WO | 2022/047041 A1 | 3/2022 | |
| WO | 2023/276525 A1 | 1/2023 | |

OTHER PUBLICATIONS

International Search Report with Written Report for PCT/JP2023/ 019875, filed May 29, 2023.
Annals of The Japanese Respiratory Society, Apr. 10, 2022, vol. 11 (3 pages).

* cited by examiner

COVID-19:
OMICRON STRAIN
PCR-POSITIVE PEOPLE
n=50

◆DISCOMFORT IN PHARYNX REGIONS:
  NO DIFFERENCE BETWEEN RIGHT AND LEFT
■DISCOMFORT IN PHARYNX REGIONS:
  DIFFERENCE BETWEEN RIGHT AND LEFT IS PRESENT
※NUMERICAL VALUE IS DIFFERENCE VALUE
  BETWEEN RIGHT EIFU TEMPERATURE
  AND LEFT EIFU TEMPERATURE

SCREENING APPARATUS FOR COLD SYNDROME-POSITIVE PEOPLE

FIELD

This invention relates to a screening apparatus that evaluates whether a person determined by PCR test to be infected with a virus such as coronavirus that causes a cold syndrome (hereinafter referred to as "cold syndrome-positive person/people") are true positive person or not, and notifies the information of severity, which is an indicator of a start or an amount of medication.

BACKGROUND

For determination of whether or not to administer medication or determination of the amount of medication for a cold syndrome-positive person, an axillary temperature is usually measured and then the medication is determined to be needed when the axillary temperature exceeds a threshold (e.g., 37.5° C.), and the amount of the medication is increased when the axillary temperature is even higher (e.g., over 38.0° C.).

However, the state of the disease varies depending on a variety of factors such as the characteristics of the pathogen itself, the ways of person-to-person contact in a population, physical individual differences in immunity and resistance to the pathogen, behavioral changes, normalcy bias, and external environments.

For example, a result of measuring axillary temperatures of 50 people determined to be positive by PCR test has represented a minimum value of 36.0° C., a maximum value of 38.7° C., and an average value of 36.7° C. However, cases have been observed where some people are diagnosed as likely to be true positive people and as requiring an immediate start of medication even if the temperature is below the average value, or conversely some people are diagnosed as pseudo positive people and as to be better followed up even if the temperature exceeds the average value.

Patent Literature 1 (Japanese Patent No. 6951526) describes provision of two heat conductive elements (122) on skin fitting portions (112) corresponding to the skin behind the user's ears to contact the portion with the skin behind the ears for collecting body temperature data (see paragraph 0047 and FIGS. 4 and 5), and an access control system for performing access control by acquiring the user's historical body temperature data (see paragraph 0112). Patent Literature 2 (Japanese Patent No. 5656978) describes a device for measuring body temperature distribution that can display the body temperature of the back of the head below the right and left ears and test a state of body distortion based on the balance of the body temperature (see paragraph 0024 and FIG. 1).

CITATION LIST

Patent Literature

[Patent Literature 1] Japanese Patent No. 6951526 (Japanese Unexamined Patent Application Publication No. 2021-171623)
[Patent Literature 2] Japanese Patent No. 5656978 (International Publication No. WO 2011/125349)

SUMMARY

Technical Problem

Although the access control system described in Patent Literature 1 collects body temperature data behind the ears, how to process the data is unclear, and although the device for measuring body temperature distribution described in Patent Literature 2 can test a state of body distortion based on a balance of a body temperature, the relationship between the balance of the body temperature and the state of the body distortion is unclear.

Furthermore, these techniques are not for evaluating whether or not cold syndrome-positive people are true positive people and performing screening. Furthermore, there is no description and suggestion about combining the balance between the right and left body temperatures and predetermined subjective symptoms of a subject, and evaluating and notifying the state of the subject.

The present invention has been made to provide reference information for determining instructions or an amount of medication to each cold syndrome-positive person by accurately evaluating whether or not each cold syndrome-positive person is a true positive person based on a surface temperature of right and left EIFU parts (an objective evaluation item) measured for and subjective symptoms of discomfort in right and left pharynx regions (a subjective evaluation item) heard from the cold syndrome-positive people and notifying the evaluation results.

Solution to Problem

A screening apparatus for cold syndrome-positive people according to claim 1 includes:
  a right temperature measuring part and a left temperature measuring part that measure surface temperatures of a right EIFU and a left EIFU of a cold syndrome-positive person, respectively;
  an input unit of left/right discomfort to which right discomfort information on discomfort in a right pharynx region and left discomfort information on discomfort in a left pharynx region perceived by the cold syndrome-positive person are input;
  a calculation unit of EIFU temperature difference that calculates a difference value between a surface temperature of the right EIFU measured with the right temperature measuring part and a surface temperature of the left EIFU measured with the left temperature measuring part;
  a calculation unit of left/right discomfort that calculates a degree of coincidence between the right discomfort information and the left discomfort information input by the input unit of left/right discomfort;
  an evaluation unit that outputs information of severity of the cold syndrome-positive person based on the difference value calculated in the calculation unit of EIFU temperature difference and the degree of coincidence calculated in the calculation unit of left/right discomfort; and
  a reporting unit that notifies the severity of the cold syndrome-positive person based on the information of severity output from the evaluation unit, wherein
  when the difference value is a first predetermined value or more and the degree of coincidence is low, the evaluation unit outputs information of high severity indicating that the severity is high as the information of severity, and
  the first predetermined value is selected from a range of 0.8 to 1.2° C.

In the screening apparatus for cold syndrome-positive people described in claim 1, the invention according to claim 2 includes a calculation unit of EIFU average temperature that calculates an average value of the surface temperature of the right EIFU measured with the right temperature measuring part and the surface temperature of the left EIFU measured with the left temperature measuring part, wherein when the difference value is a second predetermined value or more, the degree of coincidence is high, and the average value is a fourth predetermined value or more, or when the difference value is a third predetermined value or more and less than the first predetermined value, the degree of coincidence is low, and the average value is the fourth predetermined value or more, the evaluation unit outputs information of moderate severity indicating that the severity is moderate as the information of severity, and the second predetermined value is a value selected from a range of 0.4 to 0.6° C., the third predetermined value is a value selected from a range of 0.2 to 0.3° C., and the fourth predetermined value is a value selected from a range of 34 to 36° C.

Advantageous Effects of Invention

A screening apparatus for cold syndrome-positive people of the invention according to claim 1 accurately evaluates whether or not each cold syndrome-positive person is a true positive person based on a difference value of surface temperatures of right and left EIFU parts (WHO standard acupuncture point locations: TE17), which is an objective evaluation item, and a degree of coincidence between right discomfort information and left discomfort information, which is a subjective evaluation item, and notifies the evaluation results, thereby providing reference information for determining instructions or an amount of medication to each cold syndrome-positive person.

A screening apparatus for cold syndrome-positive people of the invention according to claim 2 notifies more detailed evaluation results by taking into account an average value of surface temperatures of the right and left EIFU parts, which is an objective evaluation item, in addition to the effect of the invention according to claim 1, thereby providing more detailed reference information for determining instructions or the amount of medication to each cold syndrome-positive person.

DESCRIPTION OF EMBODIMENTS

Hereinafter, embodiments of the present invention will be described with reference to Examples.

4

Example 1

Figure 1:
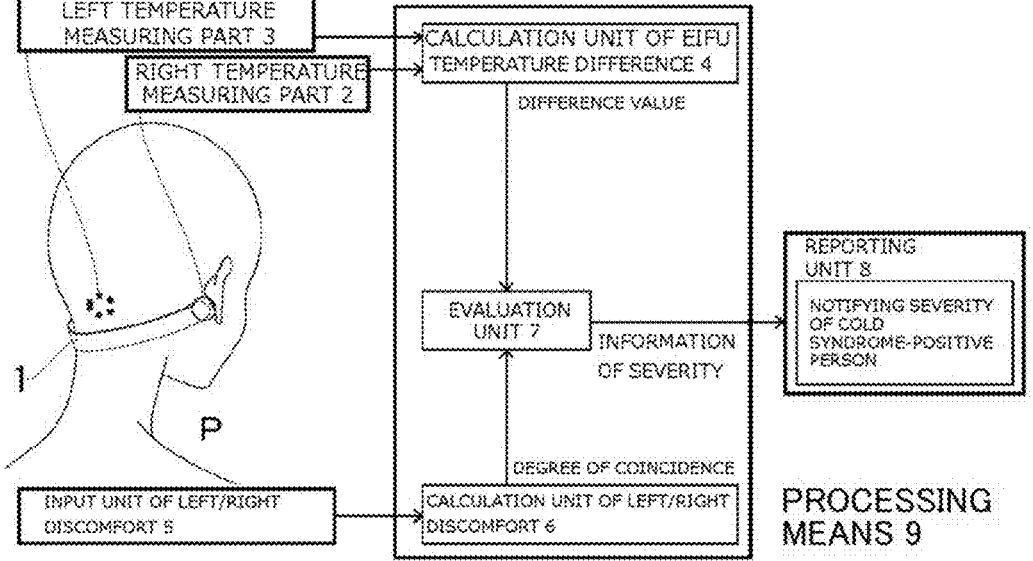
FIG. 1 is a block diagram of a screening apparatus for cold syndrome-positive people according to Example 1.

FIG. 1 is a block diagram of a screening apparatus for cold syndrome-positive people according to Example 1.

As illustrated in FIG. 1, the screening apparatus for cold syndrome-positive people according to Example 1 includes an EIFU temperature measuring means 1 having a right temperature measuring part 2 and a left temperature measuring part 3, a calculation unit of EIFU temperature difference 4 that calculates a difference value between a surface temperature of a right side EIFU (hereinafter referred to as "right EIFU temperature") measured with the right temperature measuring part 2 and a surface temperature of a left side EIFU (hereinafter referred to as "left EIFU temperature") measured with the left temperature measuring part 3, an input unit of left/right discomfort 5 to which right discomfort information on discomfort in a right pharynx region and left discomfort information on discomfort in a left pharynx region perceived by a cold syndrome-positive person P are input, a calculation unit of left/right discomfort 6 that calculates a degree of coincidence between the right discomfort information and the left discomfort information input by the input unit of left/right discomfort 5, an evaluation unit 7 that outputs information of severity of the cold syndrome-positive person P based on the difference value calculated in the calculation unit of EIFU temperature difference 4 and the degree of coincidence calculated in the calculation unit of left/right discomfort 6, and a reporting unit 8 that notifies the severity of the cold syndrome-positive person P based on the information of severity output from the evaluation unit 7.

The calculation unit of EIFU temperature difference 4, the calculation unit of left/right discomfort 6, and the evaluation unit 7 configure a processing means 9 that outputs the information of severity of the cold syndrome-positive person P upon reception of the measured value of the right EIFU temperature output from the right temperature measuring part 2, the measured value of the left EIFU temperature output from the left temperature measuring part 3, and the right discomfort information and the left discomfort information output from the input unit of left/right discomfort 5.

The EIFU temperature measuring means 1 is a means for measuring a surface temperature of an acupuncture point positioned behind the root of the ear (a point to be concaved when the mouth opens wide), which is called "eifu", and has the right temperature measuring part 2 and the left temperature measuring part 3 on both side of a U-shape elastic body, as illustrated in FIG. 1.

When the severity of the cold syndrome-positive person P is to be ascertained, the right EIFU temperature and the left EIFU temperature are measured by attaching the right temperature measuring part 2 on the EIFU positioned behind the root of the right ear (hereinafter referred to as "right EIFU") and, in the same manner, attaching the left temperature measuring part 3 on the EIFU positioned behind the root of the left ear (hereinafter referred to as "left EIFU") of the cold syndrome-positive person P. Then, the measured values of the measured right EIFU temperature and the left EIFU temperature are sent to the calculation unit of EIFU temperature difference 4 and the difference value between the right EIFU temperature and the left EIFU temperature is calculated.

The input unit of left/right discomfort 5 is for inputting the right discomfort information on discomfort in the right pharynx region and the left discomfort information on discomfort in the left pharynx region perceived by the cold syndrome-positive person P. The input right discomfort information and left discomfort information are sent to the calculation unit of left/right discomfort 6 and the degree of coincidence between the right discomfort information and the left discomfort information is calculated.

The difference value calculated in the calculation unit of EIFU temperature difference 4 and the degree of coincidence calculated in the calculation unit of left/right discomfort 6 are sent to the evaluation unit 7 and the information of severity of the cold syndrome-positive person P is output.

Then, the reporting unit 8 notifies whether or not the severity of the cold syndrome-positive person P is high based on the information of severity output from the evaluation unit 7, and medical professionals can determine the instructions or the amount of medication to the cold syndrome-positive person P by referring to the notified information of severity.

Figure 2:
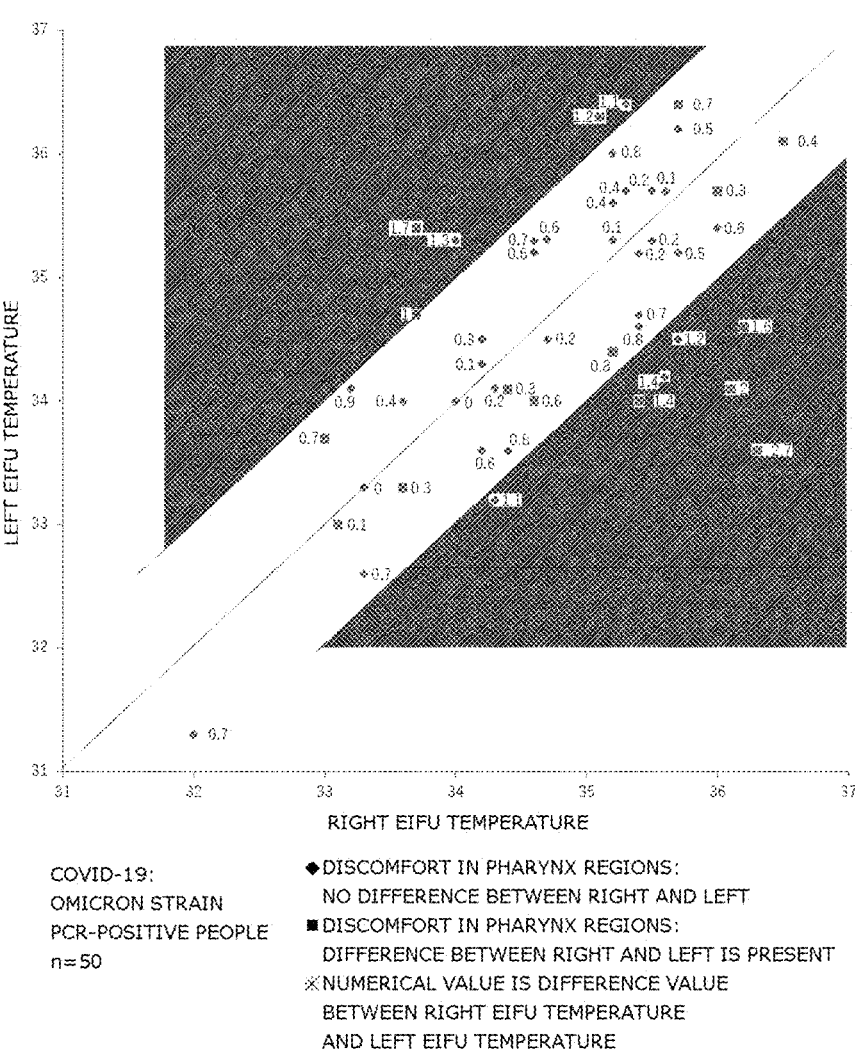
FIG. 2 is a diagram illustrating determination ranges based on a difference between right and left EIFU temperatures and a difference between discomfort in right and left pharynx regions in Example 1.

FIG. 2 is a graphical representation of the right EIFU temperature, the left EIFU temperature, the difference value between the right EIFU temperature and the left EIFU temperature, and whether or not the difference between discomfort in the right and left pharynx regions is present for 50 PCR-positive people determined to be infected with Omicron strain, which is a type of COVID-19, by PCR test.

The 50 PCR-positive people plotted in FIG. 2 were further examined by a doctor. As a result, in most cases when the difference value between the right EIFU temperature and the left EIFU temperature was small, even the PCR-positive people were diagnosed that the symptoms caused by the infection were small and to be better followed up, regardless of the difference between discomfort in the right and left pharynx regions. Conversely, in most cases when the difference value between the right EIFU temperature and the left EIFU temperature was 1° C. or more and the difference between discomfort in the right and left pharynx regions was present, the people were diagnosed that the symptoms caused by the infection were severe and immediate treatment such as medication was required.

Therefore, in Example 1, information of high severity indicating that the severity is high was output, when a person was plotted in the area illustrated with dark grey in FIG. 2 and had the difference between discomfort in the right and left pharynx regions (in FIG. 2, seven people). That is, FIG. 2 is a diagram illustrating determination ranges based on the difference between the right and left EIFU temperatures and the difference between discomfort in the right and left pharynx regions in Example 1.

Figure 3:
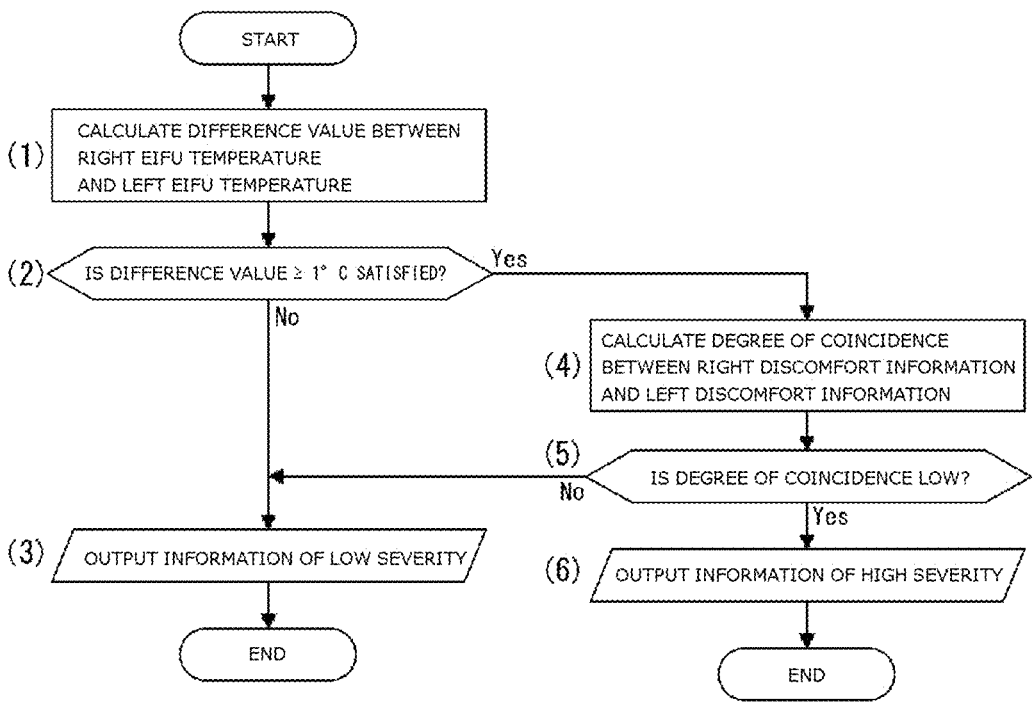
FIG. 3 is a flow diagram illustrating an algorithm in a processing means in Example 1.

FIG. 3 is a flow diagram illustrating an algorithm in the processing means 9 in Example 1 determined based on the above findings.

Upon receiving input of the measured values of the right EIFU temperature and the left EIFU temperature measured with the right temperature measuring part 2 and the left temperature measuring part 3 and further receiving input of the right discomfort information and the left discomfort information from the input unit of left/right discomfort 5, the processing means 9 starts processing, executes calculation and determination in accordance with the processing flow illustrated in (1) to (6) in FIG. 3, outputs information of low severity or the information of high severity, and ends the processing.

Next, the processing (1) to processing (6) will be described.
Processing (1) <Calculation of Difference Value>
The difference value, which is an absolute value of the difference between the measured values of the right EIFU temperature and the left EIFU temperature, is calculated.
Processing (2) <Evaluation of Difference Value>

The calculated difference value is determined whether or not the value is 1° C. or more, if No (less than 1° C.) is obtained, the flow proceeds to processing (3), if Yes (1° C. or more) is obtained, the flow proceeds to processing (4).
Processing (3) <Output of Information of Severity 1>
The information of low severity, which indicates that symptoms due to the infection are mild, is output.
Processing (4) <Calculation of Degree of Coincidence>
The degree of coincidence between the input right discomfort information and left discomfort information is calculated (if the right discomfort information and the left discomfort information are different, an L value indicating that the degree of coincidence is low is output, if the right discomfort information and the left discomfort information are similar, an H value indicating that the degree of coincidence is high is output).
Processing (5) <Evaluation of Degree of Coincidence>
The calculated degree of coincidence is determined whether or not the degree is low, if No (H value) is obtained, the flow proceeds to processing (3), if Yes (L value) is obtained, the flow proceeds to processing (6).
Processing (6) <Output of Information of Severity 2>
The information of high severity, which indicates that symptoms due to the infection are severe, is output.

Example 2

Figure 4:
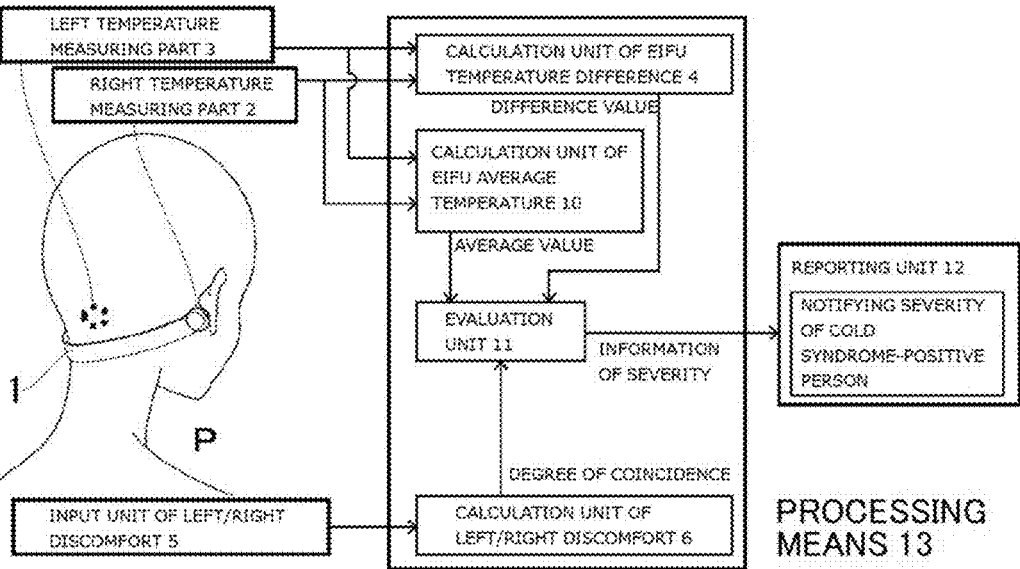
FIG. 4 is a block diagram of a screening apparatus for cold syndrome-positive people according to Example 2.

FIG. 4 is a block diagram of a screening apparatus for cold syndrome-positive people according to Example 2.

As illustrated in FIG. 4, the screening apparatus for cold syndrome-positive people according to Example 2 including a calculation unit of EIFU average temperature 10 that calculates an average temperature of the right EIFU temperature and the left EIFU temperature is different in the point where the calculation unit of EIFU temperature difference 4, the calculation unit of EIFU average temperature 10, the calculation unit of left/right discomfort 6, and an evaluation unit 11 configure a processing means 13 and in the point where a reporting unit 12 notifies a moderate degree of severity of the cold syndrome-positive person P. The EIFU temperature measuring means 1, the right temperature measuring part 2, the left temperature measuring part 3, the calculation unit of EIFU temperature difference 4, the input unit of left/right discomfort 5, and the calculation unit of left/right discomfort 6 are the same, and thus the same numbers are used and descriptions are omitted.

The difference value calculated in the calculation unit of EIFU temperature difference 4, the average value calculated in the calculation unit of EIFU average temperature 10, and the degree of coincidence calculated in the calculation unit of left/right discomfort 6 are sent to the evaluation unit 11, and the information of severity of the cold syndrome-positive person P is output.

Then, the reporting unit 12 notifies whether the severity of the cold syndrome-positive person P is high, moderate, or low based on the information of severity output from the evaluation unit 11, and medical professionals can determine the instructions or the amount of medication to the cold syndrome-positive person P by referring to the notified information of severity.

Figure 5:
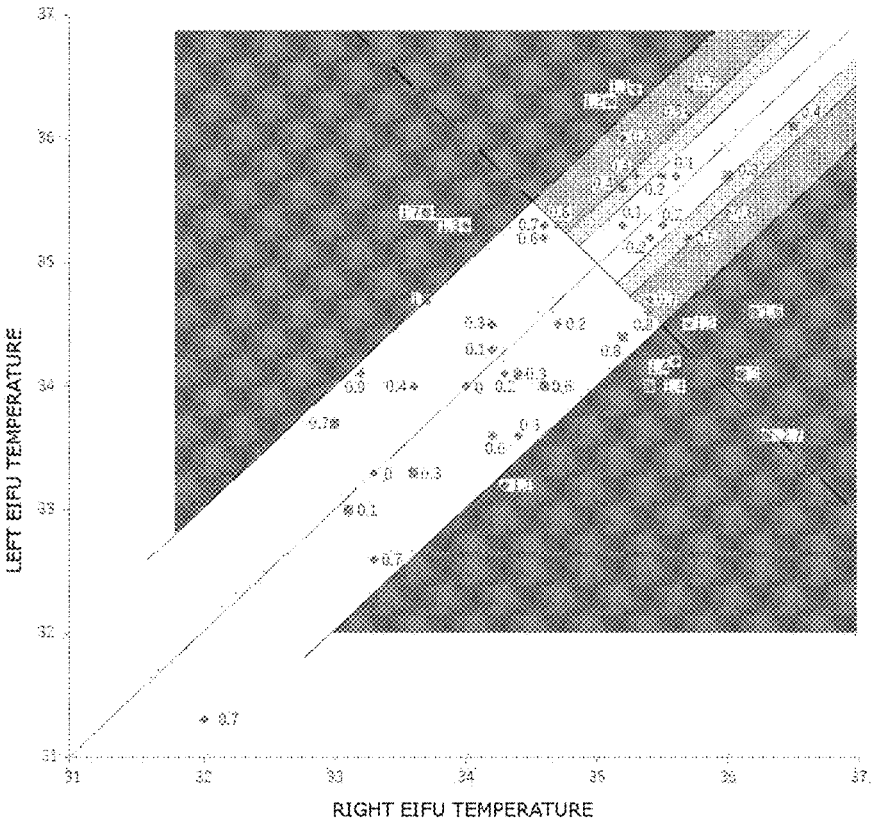
FIG. 5 is a diagram illustrating determination ranges based on the difference between the right and left EIFU temperatures and the difference between discomfort in the right and left pharynx regions in Example 2.

In the same manner as in FIG. 2, FIG. 5 is a graphical representation of the right EIFU temperature, the left EIFU temperature, the difference value between the right EIFU temperature and the left EIFU temperature, and whether or not the difference between discomfort in the right and left pharynx regions is present for 50 PCR-positive people determined to be infected with Omicron strain, which is a type of COVID-19, by PCR test.

The 50 PCR-positive people plotted in FIG. 5 were examined in detail by a doctor. As a result, in most cases when the difference value between the right EIFU temperature and the left EIFU temperature was extremely small, even the PCR-positive people were diagnosed that the symptoms caused by the infection were mild and to be better followed up, regardless of the difference between discomfort in the right and left pharynx regions. Conversely, in most cases when the difference value between the right EIFU temperature and the left EIFU temperature was 1° C. or more and the difference between discomfort in the right and left pharynx regions was present, the people were diagnosed that the symptoms caused by the infection were severe and immediate treatment such as medication was required.

Furthermore, it was found that when the difference value between the right EIFU temperature and the left EIFU temperature was 0.5° C. or more, the difference between discomfort in the right and left pharynx regions was not present, and the average temperature of the right EIFU temperature and the left EIFU temperature was 35° C. or more, or when the difference value was 0.3° C. or more and less than 1° C., the difference between discomfort in the right and left pharynx regions was present, and the average temperature was 35° C. or more, the people were diagnosed that the symptoms caused by the infection were moderate and home treatment was required.

Therefore, in Example 2, not only the information of high severity indicating that the severity is high was output when a person was plotted in the area illustrated with dark grey in FIG. 5 and had the difference between discomfort in the right and left pharynx regions, but also information of moderate severity indicating that the severity was moderate was output when a person was plotted in the areas illustrated with light grey and dark grey and had no difference between discomfort in the right and left pharynx regions (in FIG. 5, eight people) or when a person was plotted in the areas illustrated with lighter grey and light grey and had the difference between discomfort in the right and left pharynx regions (in FIG. 5, three people). That is, FIG. 5 is a diagram illustrating determination ranges based on the difference between the right and left EIFU temperatures and the difference between discomfort in the right and left pharynx regions in Example 2.

Figure 6:
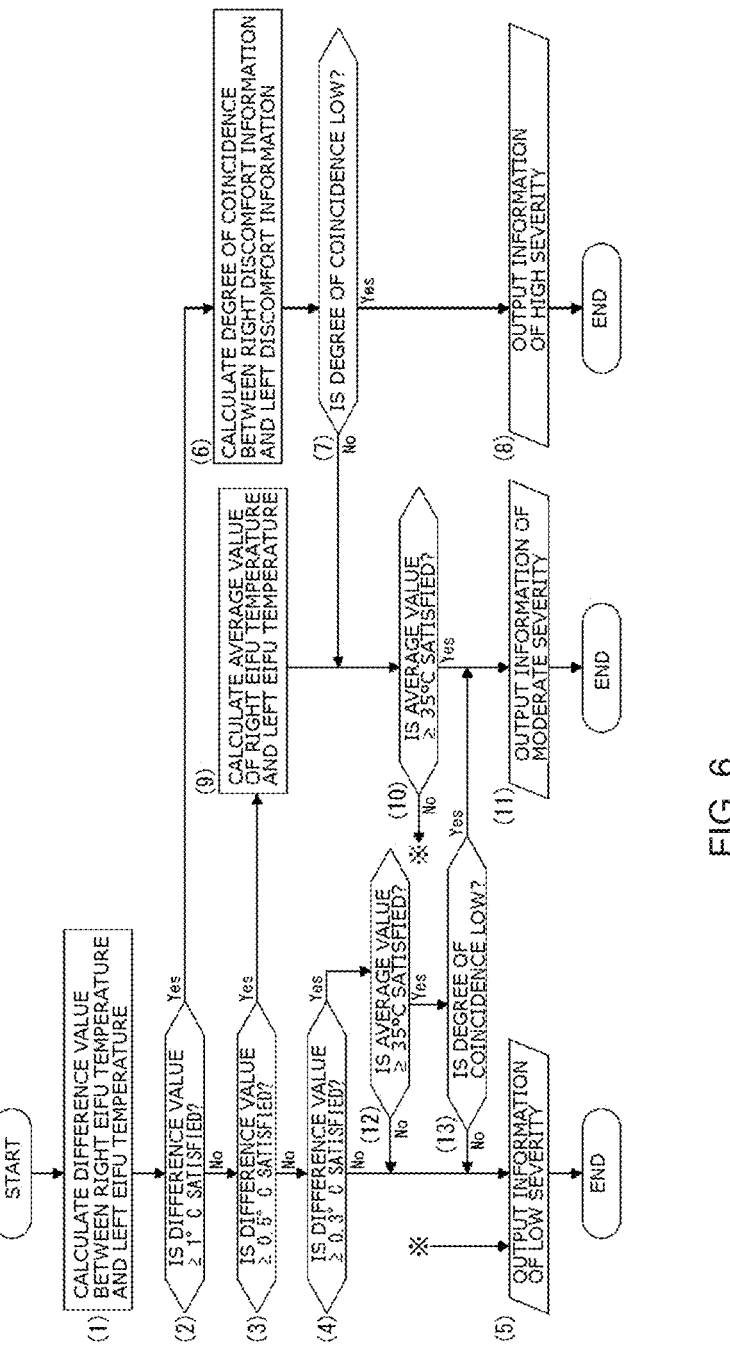
FIG. 6 is a flow diagram illustrating an algorithm in a processing means in Example 2.

FIG. 6 is a flow diagram illustrating an algorithm in the processing means 13 in Example 2 determined based on the above findings.

Upon receiving input of the measured values of the right EIFU temperature and the left EIFU temperature measured with the right temperature measuring part 2 and the left temperature measuring part 3 and further receiving input of the right discomfort information and the left discomfort information from the input unit of left/right discomfort 5, the processing means 13 starts processing, executes calculation and determination in accordance with the processing flow illustrated in (1) to (13) in FIG. 6, outputs information of low severity, information of moderate severity, or information of high severity, and ends the processing.

Next, the processing (1) to processing (13) will be described.
Processing (1) <Calculation of Difference Value>
The difference value, which is an absolute value of the difference between the measured values of the right EIFU temperature and the left EIFU temperature, is calculated.
Processing (2) <Evaluation of Difference Value 1>

The calculated difference value is determined whether or not the value is 1° C. or more, if No (less than 1° C.) is obtained, the flow proceeds to processing (3), if Yes (1° C. or more) is obtained, the flow proceeds to processing (6).
Processing (3) <Evaluation of Difference Value 2>
The calculated difference value is determined whether or not the value is 0.5° C. or more, if No (less than 0.5° C.) is obtained, the flow proceeds to processing (4), if Yes (0.5° C. or more) is obtained, the flow proceeds to processing (9).
Processing (4) <Evaluation of Difference Value 3>
The calculated difference value is determined whether or not the value is 0.3° C. or more, if No (less than 0.3° C.) is obtained, the flow proceeds to processing (5), if Yes (0.3° C. or more) is obtained, the flow proceeds to processing (12).
Processing (5) <Output of Information of Severity 1>
The information of low severity, which indicates that symptoms due to the infection are mild, is output.
Processing (6) <Calculation of Degree of Coincidence>
The degree of coincidence between the input right discomfort information and left discomfort information is calculated (if the right discomfort information and the left discomfort information are different, an L value indicating that the degree of coincidence is low is output, if the right discomfort information and the left discomfort information are similar, an H value indicating that the degree of coincidence is high is output).
Processing (7) <Evaluation of Degree of Coincidence 1>
The calculated degree of coincidence is determined whether or not the degree is low, if No (H value) is obtained, the flow proceeds to processing (3), if Yes (L value) is obtained, the flow proceeds to processing (8).
Processing (8) <Output of Information of Severity 2>
The information of high severity, which indicates that symptoms due to the infection are severe, is output.
Processing (9) <Calculation of Average Value>
The average value of the input measured value of the right EIFU temperature and the measured value of the left EIFU temperature is calculated.
Processing (10) <Evaluation of Average Value 1>
The calculated average value is determined whether or not the value is 35° C. or more, if No (less than 35° C.) is obtained, the flow proceeds to processing (5), if Yes (35° C. or more) is obtained, the flow proceeds to processing (11).
Processing (11) <Output of Information of Severity 3>
The information of moderate severity, which indicates that symptoms due to the infection are moderate, is output.
Processing (12) <Evaluation of Average Value 2>
The calculated average value is determined whether or not the value is 35° C. or more, if No (less than 35° C.) is obtained, the flow proceeds to processing (5), if Yes (35° C. or more) is obtained, the flow proceeds to processing (13).
Processing (13) <Evaluation of Degree of Coincidence 2>
The calculated degree of coincidence is determined whether or not the degree is low, if No (H value) is obtained, the flow proceeds to processing (5), if Yes (L value) is obtained, the flow proceeds to processing (11).

Modification examples related to the screening apparatuses for cold syndrome-positive people in Examples 1 and 2 are listed below.

(1) In Examples 1 and 2, the right discomfort information and the left discomfort information are input by the input unit of left/right discomfort 5. As an input mode, input of either of two options of discomfort and no discomfort, or three options of intense feeling of discomfort, moderate feeling of discomfort, and no feeling of discomfort facilitates the calculation of the degree of coincidence between the right discomfort information and the left discomfort information by the calculation unit of left/right discomfort 6. Furthermore, there is a possibility that use of the three options enables the level of the degree of coincidence to be set into three or more stages and enables more detailed evaluation.

(2) In Examples 1 and 2, the reporting units 8 and 12 notifies the severity of the cold syndrome-positive person P. As a reporting mode, at least one can be appropriately selected from, for example, displaying on a display, lighting up, turning off, and blinking of an LED, voice from a speaker, an earphone, and the like.

Furthermore, for the display on a display, not only the severity but instructions or a guideline on an amount of medication for the cold syndrome-positive person P may also be displayed.

(3) In the processing means 9 in Example 1, the calculated difference value is determined whether or not the value is 1° C. or more in processing (2), if No (less than 1° C.) is obtained, the flow proceeds to processing (3), if Yes (1° C. or more) is obtained, the flow proceeds to processing (4). However, a threshold of the difference value is expected to vary depending on the type of cold syndromes, and it is thus better to select a first predetermined value for the threshold from the range of 0.8 to 1.2° C.

(4) In the processing means 13 in Example 2, the calculated difference value is determined whether or not the value is 1° C. or more in processing (2), if No (less than 1° C.) is obtained, the flow proceeds to processing (3), if Yes (1° C. or more) is obtained, the flow proceeds to processing (6). However, in the same manner as in the above modification example (3), it is better to select the first predetermined value for the threshold of the difference value from the range of 0.8 to 1.2° C.

Furthermore, the calculated difference value is determined whether or not the value is 0.5° C. or more in processing (3), if No (less than 0.5° C.) is obtained, the flow proceeds to processing (4), if Yes (0.5° C. or more) is obtained, the flow proceeds to processing (9). However, from the same reason as in the above modification example (3), it is better to select a second predetermined value for the threshold of the difference value in processing (3) from the range of 0.4 to 0.6° C.

Furthermore, the calculated difference value is determined whether or not the value is 0.3° C. or more in processing (4), if No (less than 0.3° C.) is obtained, the flow proceeds to processing (5), if Yes (0.3° C. or more) is obtained, the flow proceeds to processing (12). However, from the same reason as in the above modification example (3), it is better to select a third predetermined value for the threshold of the difference value in processing (4) from the range of 0.2 to 0.3° C.

In addition, the calculated average value is determined whether or not the value is 35° C. or more in processing (10), if No (less than 35° C.) is obtained, the flow proceeds to processing (5), if Yes (35° C. or more) is obtained, the flow proceeds to processing (11), and the calculated average value is determined whether or not the value is 35° C. or more in processing (12), if No (less than 35° C.) is obtained, the flow proceeds to processing (5), if Yes (35° C. or more) is obtained, the flow proceeds to processing (13). However, a threshold of the average value is also expected to vary depending on the type of cold syndromes, and it is thus better to select a fourth predetermined value for the threshold of the average values in processing (10) and processing (12) from the range of 34 to 36° C.

REFERENCE SIGNS LIST

1 EIFU temperature measuring means
2 Right temperature measuring part
3 Left temperature measuring part
4 Calculation unit of EIFU temperature difference
5 Input unit of left/right discomfort
6 Calculation unit of left/right discomfort
7, 11 Evaluation unit
8, 12 Reporting unit
9, 13 Processing means
P Cold syndrome-positive person

The invention claimed is:

1. A screening apparatus for cold syndrome-positive people comprising:

an EIFU temperature measuring means which is a means for measuring a surface temperature of an acupuncture point positioned behind the root of the ear called "EIFU" of a cold syndrome-positive person who has tested positive for a virus in a polymerase chain reaction (PCR) test, and wherein the EIFU temperature measuring means comprises a U-shaped elastic body, a right temperature measuring sensor positioned on a distal end of the U-shape capable of measuring surface temperature of the right EIFU, and a left temperature measuring-sensor positioned on the other distal end of the U-shape capable of measuring surface temperature of the left EIFU;

an input means of left/right discomfort to which right discomfort information on discomfort in a right pharynx region and left discomfort information on discomfort in a left pharynx region perceived by the cold syndrome-positive person are input on a computing device;

a calculation means of EIFU temperature difference that calculates a difference value between a surface temperature of the right EIFU measured with the right temperature measuring-sensor and a surface temperature of the left EIFU measured with the left temperature measuring sensor;

a calculation means of left/right discomfort that calculates a degree of coincidence between the right discomfort information and the left discomfort information input by the input-means of left/right discomfort;

an evaluation means that outputs information of severity of the cold syndrome-positive person based on the difference value calculated in the calculation means of EIFU temperature difference and the degree of coincidence calculated in the calculation means of left/right discomfort; and a reporting means that notifies the severity of the cold syndrome-positive person based on the information of severity output from the evaluation means, wherein when the difference value is a first predetermined value or more and the degree of coincidence is low, the evaluation means outputs information of high severity indicating that the severity is high as the information of severity, and the first predetermined value is selected from a range of 0.8 to 12° C.

2. The screening apparatus for cold syndrome-positive people according to claim 1, further comprising a calculation means of EIFU average temperature that calculates an average value of the surface temperature of the right EIFU measured with the right temperature measuring sensor and calculates an average value of the surface temperature of the left EIFU measured with the left temperature measuring sensor, wherein when the difference value is a second predetermined value or more, the degree of coincidence is high, and the average value is a fourth predetermined value or more, or when the difference value is a third predetermined value or more and less than the first predetermined value, the degree of coincidence is low, and the average value is the fourth predetermined value or more, the evaluation unit means outputs information of moderate severity indicating that the severity is moderate as the information of severity, and the second predetermined value is a value selected from a range of 0.4 to 0.6° C., the third predetermined value is a value selected from a range of 0.2 to 0.3 C, and the fourth predetermined value is a value selected from a range of 34 to 36° C.

\* \* \* \* \*